United States Patent [19]

Ash

[11] Patent Number: 4,914,819
[45] Date of Patent: Apr. 10, 1990

[54] EATING UTENSIL FOR INDICATING WHEN FOOD MAY BE EATEN THEREWITH AND A METHOD FOR USING THE UTENSIL

[76] Inventor: Stephen R. Ash, 3736 Pershing, Lafayette, Ind. 47905

[21] Appl. No.: 352,977

[22] Filed: May 17, 1989

[51] Int. Cl.⁴ ..................... A47J 43/00; A47J 43/28; G04F 5/00; G04F 1/04
[52] U.S. Cl. ........................................ 30/147; 30/141; 368/93; 368/95
[58] Field of Search ................... 30/147, 141; 446/15; 364/714; 368/54, 93, 95, 152

[56] References Cited

U.S. PATENT DOCUMENTS

| | | | |
|---|---|---|---|
| 51,748 | 12/1865 | Pearson | 30/123 |
| 671,247 | 4/1901 | Super | 30/141 |
| 1,206,585 | 11/1916 | Parrahm | 30/123 |
| 1,619,878 | 3/1927 | Morgan et al. | 30/123 |
| 1,988,379 | 1/1935 | Gilles | 30/123 |
| 2,644,890 | 7/1953 | Hollihan | 368/93 |
| 2,714,927 | 8/1955 | Stern et al. | 368/95 |
| 2,795,043 | 6/1957 | Fleischer | 30/141 |
| 3,465,516 | 9/1969 | Von Meyer | 368/95 |
| 3,510,643 | 5/1970 | File | 30/123 |
| 3,784,206 | 1/1974 | Stuss | 273/158 |
| 3,839,793 | 10/1974 | Crapio | 30/123 |
| 4,207,673 | 6/1980 | DiGirolamo et al. | 30/142 |

FOREIGN PATENT DOCUMENTS

| | | | |
|---|---|---|---|
| 268013 | 4/1950 | Switzerland | 30/123 |
| 9256 | 8/1885 | United Kingdom | 30/123 |

Primary Examiner—Douglas D. Watts
Assistant Examiner—Paul M. Heyrana, Sr.

[57] ABSTRACT

A dietary control eating utensil is disclosed for indicating when food can be eaten therewith. The handle of the utensil includes a gravity-powered timing device. The device includes an elongated transparent material chamber for containing immiscible fluids having different densities such as air and mineral oil. The lighter density fluid forms a visible signal within the chamber that is moveable between the distal and proximal ends. The period associated with the movement of the visible signal depends on the different elevations of the chamber ends. The shape of the chamber along with the density of the two fluids also contributes to the time period the visible signal takes to move between the two ends of the chamber. When the air bubble moves to a predetermined position within the chamber, this indicates when the utensil may be used for consuming food.

19 Claims, 1 Drawing Sheet

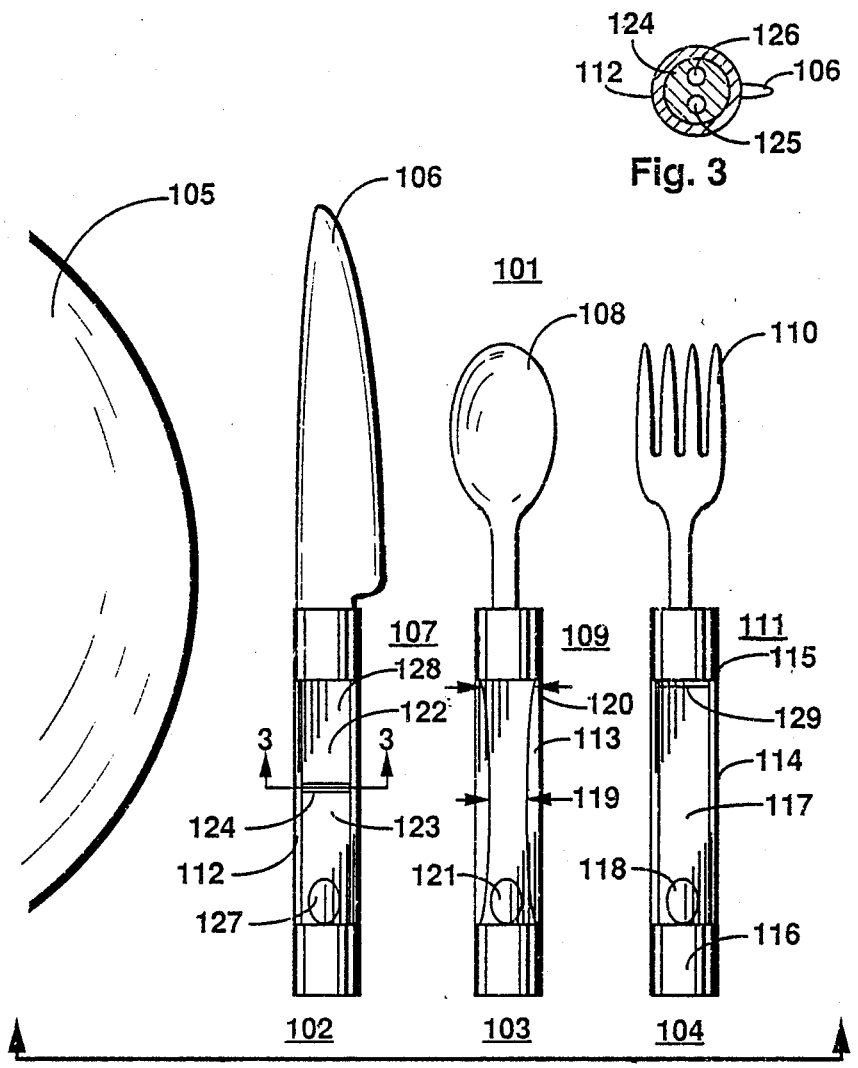
Fig. 3
Fig. 1
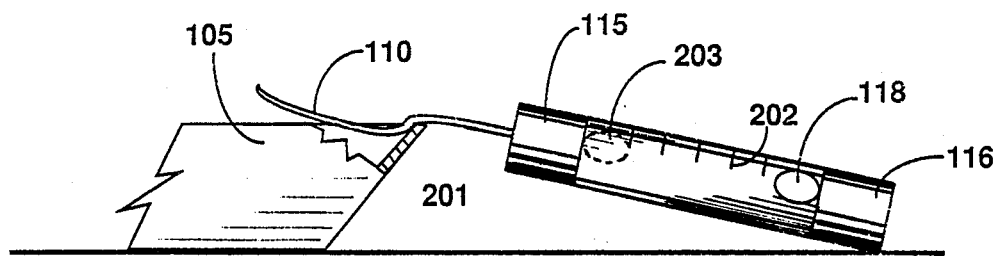
Fig. 2

EATING UTENSIL FOR INDICATING WHEN FOOD MAY BE EATEN THEREWITH AND A METHOD FOR USING THE UTENSIL

TECHNICAL FIELD

This invention relates generally to eating utensils, and in particular, to a utensil for indicating when food may be eaten therewith and a method for using the same.

BACKGROUND OF THE INVENTION

In many developed countries, up to 30% of the population is significantly overweight and obese. Obesity is highly correlated to a number of health problems including hypertension, diabetes, mellitus, hyperlipidemia, cardiovascular disease, and various psychological problems.

Causes of obesity are numerous. For many, obesity starts in childhood with overfeeding and the use of food as reward for good behavior. Lack of nutritional education leads to a lifelong choice of high calorie foods of low nutritional value. A sedentary existence may follow a childhood of little activity or participation in nonaerobic sports.

As dining has become a solitary rather than a family or social event, it has become more rapid. Rapid eating is also a major cause of obesity. Although the intestinal tract secretes several hormones to indicate to the brain that sufficient food has been ingested, these and other psychological mechanisms require approximately 10-15 minutes to indicate such to the brain. As a result, a rapid eater can consume may excess calories before these mechanisms signal a "full feeling" to the brain.

Classic dieting techniques have typically failed to permanently reduce the weight of many overweight people. One such approach is to consume less calories than expended. This typically includes a "crash" diet with relatively unpallible, low-calorie foods and an exercise program to increase aerobic metabolism, consume body fat stores and change metabolic patterns.

Another approach is to teach the patient to measure the weight or volume of each food to be eaten and then multiplying the measured quantity by a published value of calories per unit weight or volume. When the total calorie intake reaches a predetermined amount, the person should stop eating.

These dieting techniques typically fail, even after weight loss, due to the person returning to old eating habits and regaining lost weight.

As a result, other dieting techniques have been developed to permanently change eating habits. These include choosing nutritionally proper foods, engaging in strenuous activity to increase calorie use and decrease appetite, and substituting other emotionally satisfying rewards besides food. However, simply learning to eat slowly allows the body's feedback mechanisms to naturally limit food intake.

A number of prior art devices have been suggested for indicating a minimum desired time between bites of food. These devices include for example a simple, standalone timer that is reset by the diner after each bite of food to signal when the next bite may be eaten. Another device includes an electronic timer enclosed within the handle of an eating utensil. The diner resets the electronic device after each bite and weights for a light to appear after a time period determined by the components of the timer. The motivated dieter waits for the appropriate light signal before using the utensil to ingest the next bite of food. However, this utensil has a number of problems. First, the distal end of the utensil must be removed from the handle for cleaning. A battery included in the handle makes the utensil relatively large, unattractive, and clumsy to handle. Furthermore, replacement of the battery or electrical components is inconvenient and costly.

SUMMARY OF THE INVENTION

The foregoing problems are solved and a technical advance is achieved in an illustrative eating utensil for indicating when food may be eaten therewith by a visible signal viewable from an elongated chamber included in the handle of the utensil. The utensil includes an instrumentality such as a fork, spoon, or knife for engaging and conveying the food and a handle for manipulating the instrumentality. Included in the handle is an elongated chamber for containing a pair of immiscible fluids having different densities. Illustratively, a large volume of mineral oil occupying most of the chamber comprises one of the fluids, whereas a much smaller volume of air comprises the other fluid. The air forms a bubble or visible signal in the mineral oil, which is moveable between the ends of the chamber when one end is elevated above the other. Movement of the air bubble forms one position to another within the chamber takes a predetermined time period and advantageously indicates when a bite of food may be eaten with the use of the utensil.

The method for using the utensil includes positioning the utensil with the instrumentality resting on a dish and the handle resting next to the dish, for example on a table, with the distal end of the chamber elevated above the proximal end. To take a bite of food, the user simply lifts the utensil to engage and convey the bite of food. This elevates the proximal end of the elongated chamber above the distal end, thereby causing the air bubble therein to move towards the proximal end. Elevating the proximal end of the utensil for extended periods of time such as with engaging and conveying large bites of food causes the air bubble to move to the extreme proximal end of the chamber. This advantageously increases the amount of time the air bubble will take to move back to the distal end or a predetermined position marked along the chamber when the instrumentality is repositioned on the edge of the plate.

After the utensil is so positioned on the plate with the distal end of the chamber elevated above the proximal end, the diner waits until the air bubble moves to a predetermined position along the elongated chamber before using the utensil again to take the next bite of food. A timing interval between bites of food is advantageously controlled by the elevation of the utensil on the plate as well as how long the proximal end of the utensil is elevated between bites of food. Holding the utensil with the proximal end upwards for extended periods of time while eating causes the air bubble to move to the extreme proximal end of the chamber, thereby increasing the amount of time it will take for the bubble to reach the extreme distal end of the chamber. Various positions marked along the chamber may also be utilized by the user to indicate various minimum time periods after positioning the utensil on the plate.

Illustratively, the chamber comprises a cylinder of transparent material for viewing movement of the air bubble between the two ends of the chamber. In one illustrative embodiment, at least one of the ends includes a colored material for reflecting the color outside of the transparent chamber as the air bubble approaches the end within a predetermined distance.

Other embodiments of the chamber include a hollow cylinder with an inside diameter about the center smaller than the diameter at the ends to slow passage of the fluids between the two ends.

In yet another illustrative embodiment, the chamber includes a pair of hollow portions with a partition having upper and lower passageways between the two portions to create two streams of different fluid flow and also slow passage of the different density fluids between the two portions.

The movement of the different density fluids within the chamber of each embodiment comprises a timing period or an interval of time which the user should wait between taking bites of food. Positions marked about either end of the chamber may be utilized to signal the start and finish of any desired interval of time that the moveable fluid should take in moving from one position to another within the chamber.

The eating utensil of this invention advantageously uses the forces of gravity to power the moveable fluids within the chamber, thereby advantageously foregoing the need of a separate power source. The shape and length of the chamber along with the choice of a partition within the chamber may be utilized to aesthetically enhance the appearance of the eating utensil. With the fluids contained within the chamber, the utensil may be also conveniently cleaned without having to remove the instrumentality from the handle of the utensil.

BRIEF DESCRIPTION OF THE DRAWING

FIG. 1 depicts a place setting of the eating utensils of the present invention for indicating when food may be eaten;

FIG. 2 depicts one of the eating utensils of FIG. 1 positioned on the edge of a plate with the distal end of the utensil elevated to move the visible signal thereto; and FIG. 3 depicts a cross-sectional view of another of the eating utensils of FIG. 1 along the lines 3—3.

DETAILED DESCRIPTION

Depicted in FIG. 1 is a place setting 101 of eating utensils 102–104 positioned next to a dish such as plate 105. Each of eating utensils 102–104 includes an instrumentality for engaging and conveying food and a handle for manipulating the instrumentality. The instrumentality of eating utensil 102 comprises a knife blade 106 with handle 107 affixed thereto in a well-known manner. The instrumentality of eating utensil 103 comprises a spoon 108 with handle 109 affixed thereto. The instrumentality of eating utensil 104 comprises a set of prongs 110, commonly referred to as a fork, with handle 111 affixed thereto. Instrumentalities 106, 108 and 110 are all well-known devices for engaging and conveying food. Each of handles 107, 109 and 111 includes a gravity-powered timing device that is utilized when eating food for indicating that a minimum time period has elapsed and that the next bite of food may be taken. When utilized in a dietary control program, the timing device of the eating utensil establishes a minimum time period between bites of food to slow down the eating cycle of the user. This slows down the consumption rate of food and permits the well-known mechanisms of the body to signal a "full feeling." This advantageously allows the natural mechanisms of the user's body to control the eating process and to prevent the excess intake of unnecessary and harmful calories that typically lead to an overweight condition and accompanying health problems.

The gravity-powered timing device or timer included in handles 107, 109, and 111 of the utensils comprises an elongated chamber 112, 113, and 114, respectively. In this preferred embodiment, the elongated chamber comprises a hollow cylinder of transparent plastic material for viewing a visible signal or formation at a predetermined position along the chamber for indicating when food may be eaten. Elongated chamber 114 has a distal end 115 and a proximal end 116 for containing therein immiscible fluids 117 and 118 having different densities. Heavier density fluid 117, such as well-known mineral oil, occupies the majority of the hollow transparent cylinder. The lighter density fluid 118 occupies a much smaller volume of the chamber. This lighter density fluid forms the visible signal or formation and appears as a bubble in the more dense fluid. Other combinations of different density fluids are contemplated such as air and water, water and petroleum, etc.

The method of using the utensil simply involves lifting the utensil up by the handle thereof to engage or convey food. In this process, proximal end 116 of the handle is elevated above distal end 115. As a result, the lighter density air bubble moves toward the extreme proximal end of the chamber and stops thereat as shown in FIG. 1 after a predetermined time period.

After consuming a bite of food, the user positions the utensil with the instrumentality such as prongs 110 resting on the edge of plate 105. Proximal end 116 of the chamber and handle are positioned next to the plate on table surface 201 as shown in FIG. 2. In such position, the distal end of the chamber is elevated above the proximal end. As a result, the lighter density fluid, air bubble 118, moves toward the distal end 115 of the handle at a rate dependent upon the density of the two fluids, the internal shape or diameter of the chamber, and the difference in elevation between the distal and proximal ends of the chamber. A number of graduation positions 202 are marked along the length of the transparent chamber for indicating different time periods as the air bubble moves toward the extreme distal end. The user may wait until air bubble 118 reaches the extreme distal end as shown by phantom line air bubble 203 before using the utensil to take the next bite of food. The user should wait at least 6–12 seconds between each bite of food to permit the satiety mechanisms to signal a "full feeling." Depending on the height of the plate, air bubble 118 may take longer than the minimum 6–12 second time period to reach the distal end. Graduation positions 202 marked along the chamber permit the user to select a time period less than that for the air bubble to reach the extreme distal end. After the air bubble reaches the extreme distal end or one of the graduation positions, the user lifts the utensil from the plate to take a bite of food. Lifting the proximal end of the utensil above the distal end of the chamber, causes the bubble to once again move toward proximal end 116. The user elevates the proximal end of the chamber to move the air bubble to the extreme proximal end of the chamber or to one of the graduation positions marked along the chamber while taking a bite of food. This moves the air bubble to a start position for resetting the timing interval between bites of food. After taking a bite of food, the user repositions the utensil on the edge of the plate to restart the movement of the air bubble toward the distal end. This also restarts the time interval that the user should wait before taking the next bite of food.

Eating utensil 104 has been described with a cylindrical chamber within handle 111. However, to make the movement of the air bubble or other less dense fluid more interesting, other figurations of the chamber are contemplated as shown by utensils 102 and 103 in FIG. 1. Elongated chamber 113 of utensil 103 includes a cylindrical chamber wherein the inside diameter 119 about the middle of the chamber is less than the inside diameter 120 at the distal and proximal ends of the chamber. Small inside diameter 119 causes the less dense fluid 121 to take a longer period of time to reach the distal end than if the inside diameter of the cylinder were uniform.

With respect to eating utensil 102, elongated chamber 112 includes two portions 122 and 123 separated by partition 124 positioned across the approximate middle of the chamber. The partition includes two passageways 125 and 126 of which one such as passageway 126 is elevated higher than the other with the utensil resting on the plate. This is depicted in FIG. 3 which is a cross-sectional view of chamber 112 taken along the lines 3—3 in FIG. 1. As a result, this forces the two density fluids 127 and 128 into small streams as they pass between the two portions. The direction of flow depends on which end of the chamber is elevated above the other. The passageway reduces the flow rate of the fluids and makes a more visible interaction between the fluids as they flow past one another.

Another alteration of the chamber includes positioning a colored disk 129 at the extreme distal end of chamber 114. The color of the disk is visible only when the lighter density fluid approaches the disk within a predetermined distance. Otherwise, the angle of incidence is too low to allow light to exit from the transparent material of the chamber without an internal reflecting surface.

To make the movement of the lighter density fluid even more interesting, the optical density of the heavier fluid may be similar to that of the transparent plastic material of the chamber. As a result, the interface between the heavier density fluid in the handle appears invisible. Thus, the lighter density fluid or bubble appears to move through the center of the chamber without any obvious restraint. Furthermore, the edges of the bubble are highly reflective creating interesting reflections of any colored surface near the utensil. Including colored dye in one or both of the fluids also permits additional interesting visual effects directing the user's attention to optical phenomena within the eating utensil. This further diminishes attention on food, further reducing the rate of eating.

The eating utensil as described is comprised of materials which are readily washed by hand or by machine. As a result, no maintenance of the utensil is required other than cleaning.

While the invention has been illustrated and described in detail in the drawing and foregoing description, the same is to be considered illustrative and not restrictive in character. It being understood that only the preferred embodiment has been shown along with several alternative embodiments and that all changes and modifications that come within the spirit of the invention are desired to be protected. In addition, it is contemplated that an aperture may be formed in the elongated chamber for replacing the different density fluids with other combinations or colors of different density fluids to provide different timing intervals as well as visual effects.

What is claimed is:

1. An eating utensil for indicating when food may be eaten therewith, comprising:
   an instrumentality for engaging said food; and
   a handle for manipulating said instrumentality and including an elongated chamber for viewing a visible signal at a predetermined position along said chamber for indicating when said food may be eaten, said chamber having first and second ends for containing first and second immiscible fluids having different densities, one of said fluids forming said visible signal and moveable to said predetermined position when one of said ends is elevated above the other.

2. The eating utensil of claim 1 further comprising said first and second immiscible fluids having different densities.

3. The eating utensil of claim 2 wherein said first fluid comprises air.

4. The eating utensil of claim 3 wherein said second fluid comprises mineral oil.

5. The eating utensil of claim 2 wherein said one fluid forms a second visible signal at a second predetermined position along said chamber for positioning said instrumentality on a dish and said handle next to said dish, said one fluid being moveable to said second position when said other end of said chamber is elevated above said one end.

6. The eating utensil of claim 1 wherein said chamber comprises a cylinder of transparent material.

7. The eating utensil of claim 6 wherein at least one of said ends includes a material having a predetermined color for reflecting said color outside of said transparent chamber as said one fluid approaches said at least one end within a predetermined distance.

8. The eating utensil of claim 1 wherein said chamber comprises a cylinder having a first inside diameter about said ends and a second inside diameter smaller than said first diameter about the middle of said chamber for slowing passage of said fluids between said ends.

9. The eating utensil of claim 1 wherein said instrumentality comprises a fork.

10. The eating utensil of claim 1 wherein said instrumentality comprises a spoon.

11. The eating utensil of claim 1 wherein said instrumentality comprises a knife.

12. The eating utensil of claim 1 wherein said chamber includes first and second portions and a partition with first and second passageways between said portions.

13. An eating utensil wherein a timer is provided comprising:
    first and second immiscible fluids having different densities and an elongated chamber having first and second ends for containing said fluids, one of said fluids forming a visible formation moveable to a predetermined position about one of said ends for timing said interval of time when said one end is elevated above the other, said interval of time comprising the amount of time for said formation to move from said first end to said predetermined position.

14. A dietary control fork, comprising:
    a plurality of prongs for engaging said food; and
    a handle for manipulating said prongs, said handle including an elongated cylinder having first and second ends and comprised of a transparent material for viewing a bubble at a predetermined position about said first end for indicating when said food may be eaten and also including mineral oil and air contained in said chamber, said air forming said bubble in said mineral oil, said bubble being moveable to said predetermined position at a predetermined rate, when said first end is elevated above said second end a predetermined distance, said bubble being moveable to a start position about said second end when said second end is elevated above said first end, said bubble moving from said start to said predetermined position in a predetermined period of time dependent on said first end being elevated above said second end a predetermined distance, a diameter of said cylinder, and the density of said mineral oil.

15. Method of indicating with an eating utensil when food may be eaten, said utensil having a visible formation moveable between proximal and distal ends of an elongated chamber included in a handle thereof, said utensil also including an instrumentality for manipulating said food, comprising the steps of:

positioning said utensil with said instrumentality resting on a dish and said handle resting next to said dish with said distal end of said chamber elevated above said proximal end, and waiting until said visible formation moves toward said distal end and to a predetermined position along said elongated chamber before using said utensil to engage said food.

16. The method of claim 14 further comprising lifting said utensil from said dish to manipulate said food after said visible formation reaches said predetermined position along said elongated chamber.

17. The method of claim 14 further comprising elevating said proximal end of said chamber above said distal end to move said visible formation toward said proximal end while using said utensil to engage said food.

18. The method of claim 16 further comprising waiting until said visible formation moves toward said proximal end and to a second predetermined position along said elongated chamber before repositioning said utensil on said dish.

19. The method of claim 16 further comprising repositioning said utensil on said dish after eating a bite of said food with said utensil.

* * * * *